United States Patent
Jung et al.

(12) 
(10) Patent No.: US 6,482,565 B1
(45) Date of Patent: Nov. 19, 2002

(54) PHOTORESIST CROSS-LINKER AND PHOTORESIST COMPOSITION COMPRISING THE SAME

(75) Inventors: Jae Chang Jung; Keun Kyu Kong; Myoung Soo Kim; Hyoung Gi Kim; Hyeong Soo Kim; Ki Ho Baik, all of Kyoungki-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 09/448,964

(22) Filed: Nov. 24, 1999

(30) Foreign Application Priority Data

Nov. 27, 1998 (KR) .............................. 98-51356
Feb. 22, 1999 (KR) .............................. 99-5825

(51) Int. Cl.$^7$ .............................................. G03F 7/004
(52) U.S. Cl. .................... 430/270.1; 430/325; 526/266; 526/320; 526/271; 549/347; 549/369; 549/430
(58) Field of Search .............................. 430/270.1, 325; 549/347, 369, 430; 526/266, 320, 271

(56) References Cited

U.S. PATENT DOCUMENTS

| | | | |
|---|---|---|---|
| 3,468,857 A | | 9/1969 | Graver ........................ 260/80.3 |
| 5,049,463 A | * | 9/1991 | Kato et al. ..................... 430/49 |
| 5,059,698 A | | 10/1991 | Schulthess et al. .......... 549/375 |
| 5,412,041 A | * | 5/1995 | Lesko et al. ................. 525/340 |
| 6,060,212 A | * | 5/2000 | McCulloch et al. ..... 430/270.1 |

FOREIGN PATENT DOCUMENTS

| | | |
|---|---|---|
| DE | 3714276 A1 | 11/1988 |
| EP | 0 347 381 A1 | 12/1989 |
| EP | 0 422 888 A2 | 4/1991 |
| EP | 875 789 A1 | 11/1998 |
| GB | 922747 | 4/1963 |
| JP | 4-5040054 * | 12/1970 |
| JP | 5-216294 * | 8/1993 |
| WO | WO 99/61497 | 12/1999 |

OTHER PUBLICATIONS

1970:100663 Caplus Abstract.*
1971:65746 Caplus Abstract.*
1967:10943 Caplus Abstract.*
1984:10943 Caplus Abstract.*
1972:552633 Caplus Abstract.*
1970:477088 Caplus Abstract.*
1998:604944 Caplus Abstract.*
1971:112779 Caplus Abstract of JP 45040054, Dec. 1970.*
1970:510169 Caplus Abstract to Ouchi, T. et al. Kogyo Kagaku Zasshi, 1970, 73(7), 1717–19.*
Anionic polymerizabilities of 2–vinyl–1,3–dioxolane and 2–vinyl–1,3–dioxane, Yamashita, N. et al., J. Polym.Sci., Polym.Lett.Ed., 1979, 17, 521–6.*
1994:496066 Caplus Abstract of JP 5216294, Aug. 1993.*
Chemical Abstract No. 131:337017 & JP 11315075.
Chemical Abstract No. 128:295769 & JP 10088419.
Chemical Abstract No. 118:102825 & J. Maslinska–Solich et al., React. Polym. (1992), 18(2), 159–166.
J.Maśliṅska–Solich et al., "Studies on Co(II) and Mn(II) complexex of some maleic anhydride copolymers," *Reactive Polymers*, vol. 18, 1992, pp. 159–166.

* cited by examiner

Primary Examiner—Rosemary E. Ashton
(74) Attorney, Agent, or Firm—Townsend and Townsend and Crew LLP

(57) ABSTRACT

The present invention relates to a cross-linker for use in a photoresist which is suitable for a photolithography process using KrF (248 ru), ArF (193 nm), E-beam, ion beam or EUV light source. According to the present invention, preferred cross-linkers comprise a copolymer having repeating units derived from: (i) a compound represented by following Chemical Formula 1 and/or (ii) one or more compound(s) selected from the group consisting of acrylic acid, methacrylic acid and maleic anhydride.

<Chemical Formula 1>

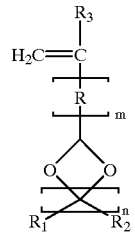

wherein, $R_1$, $R_2$ and R individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group; $R_3$ represents hydrogen or methyl; m represents 0 or 1; and n represents a number of 1 to 5.

16 Claims, 5 Drawing Sheets

PHOTORESIST CROSS-LINKER AND PHOTORESIST COMPOSITION COMPRISING THE SAME

FIELD OF THE INVENTION

The present invention relates to novel cross-linking agents ("cross-linkers") for negative photoresist compositions usable in the deep ultraviolet region of the light spectrum, a process for preparing the same, and negative photoresist composition using the same. More specifically, it relates to cross-linkers for photoresists which are suitable for photolithography processes using KrF (248 nm), ArF (193 nm), E-beam, ion beam or EUV light sources when preparing a microcircuit of a highly integrated semiconductor element, and photoresist compositions employing the same.

BACKGROUND OF THE INVENTION

Recently, chemical amplification type DUV (deep ultra violet) photoresists have proven to be useful to achieve high sensitivity in processes for preparing micro-circuits in the manufacture of semiconductors. These photoresists are prepared by blending a photoacid generator with polymer matrix macromolecules having acid labile structures.

According to the reaction mechanism of such a photoresist, the photoacid generator generates acid when it is irradiated by ultraviolet rays from the light source, and the main chain or branched chain of the polymer matrix macromolecule is cross-linked with the generated acid to form a cross-linked structure. Thus, the portion exposed to light cannot be dissolved by developing solution and remains unchanged, thereby producing a negative image of a mask on the substrate. In the lithography process, resolution depends upon the wavelength of the light source—the shorter the wavelength, the smaller the pattern that can be formed. However, when the wavelength of the light source is decreased in order to form a micro pattern [for example, in the case of using 193 nm wavelength or EUV (extremely ultraviolet) light], it is disadvantageous in that the lens of the exposing device is deformed by the light source, thereby shortening its life.

Melamine, a conventional cross-linker, has only three functional groups to cross-link with acid. Further, a large amount of acid must be generated when melamine is used as a cross-linker, because acid is consumed by the cross-linking reaction. As a result, higher energy light-exposure is required for such cross-linking agents.

In order to overcome the disadvantages described above, chemical amplification type components that cross-link with a photoresist resin and use less amounts of energy are desired. However, such chemical amplification type cross-linkers have not yet been developed.

Furthermore, in a pattern of high integrity, developing solution may be soaked into the cross-linked site, to swell up the cross-linked site. Thus, in order to form a pattern of higher integrity, the incorporation of a novel cross-linker, which performs cross-linking more elaborately, is required.

FIG. 1 shows a photoresist pattern that was formed by using a photoresist composition comprising a conventional cross-linker (J. Photopolymer Science and Technology, Vol.11, No.3, 1998, 507–512). The pattern is a 0.225 µm L/S pattern obtained by a photolithography process employing an ArF light source and a monomeric cross-linker.

As can be shown from FIG. 1, swelling occurs in a conventional photoresist pattern, so that a pattern of less than 0.225 µm L/S is difficult to obtain.

SUMMARY OF THE INVENTION

The object of the present invention is to provide a photoresist cross-linker, and a process for preparing the same.

Another object of the present invention is to provide a photoresist composition comprising the cross-linker, and a process for preparing the composition.

Still another object of the invention is to provide a semiconductor element manufactured by using the photoresist composition.

In order to achieve these objects, the present invention provides a cross-linker monomer that comprises a compound represented by following Chemical Formula 1:

<Chemical Formula 1>

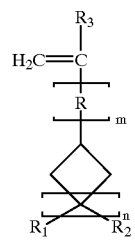

wherein, $R_1$, $R_2$ and R individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group; $R_3$ represents hydrogen or methyl; m represents 0 or 1; and n represents a number of 1 to 5.

In order to achieve another object of the present invention, a photoresist composition is provided which comprises (i) a photoresist polymer, (ii) a photoresist cross-linker as described above, (iii) a photoacid generator and (iv) an organic solvent.

DETAILED DESCRIPTION OF THE INVENTION

Figure 1:
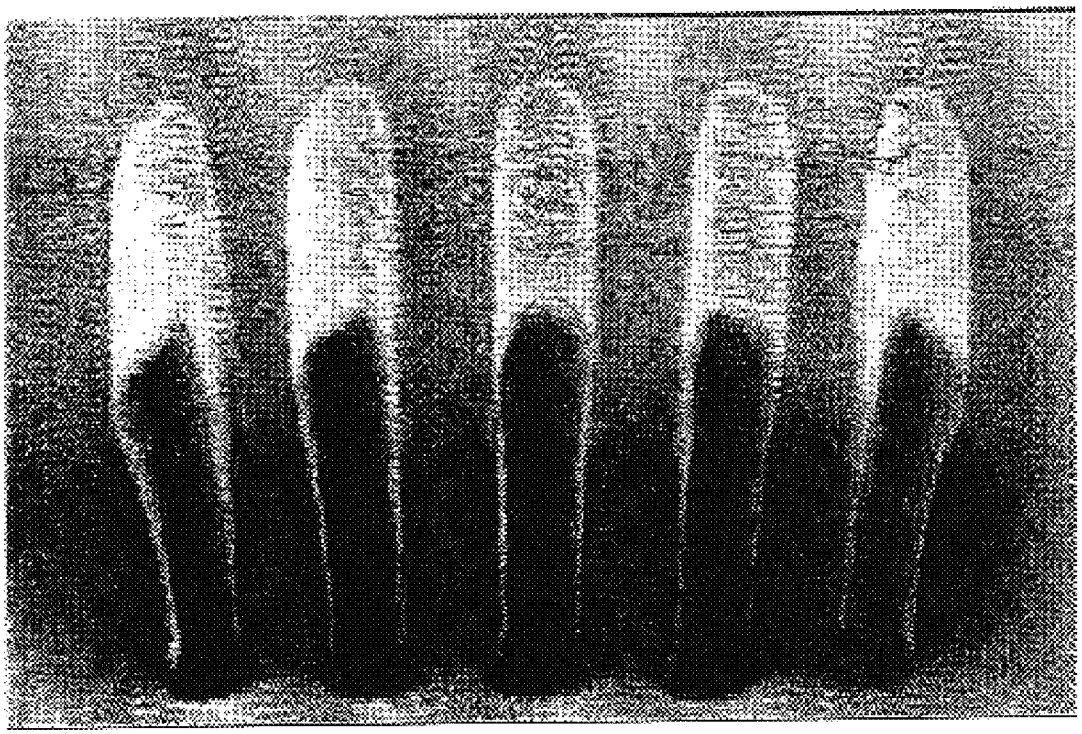
FIG. 1 shows a photoresist pattern prepared by using a conventional cross-linker.

The inventors have performed intensive studies to achieve the objects of the invention described above, and have found that compounds represented by the following Chemical Formula I have appropriate properties to serve as monomers for negative photoresist cross-linker polymers.

<Chemical Formula 1>

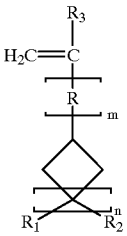

wherein, $R_1$, $R_2$ and R individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group; $R_3$ represents hydrogen or methyl; m represents 0 or 1; and n represents a number of 1 to 5.

Cross-linker polymers having repeating units derived from compounds of Chemical Formula 1 react with a photoresist resin having hydroxyl group(s) in the presence of acid, to induce a cross-linking reaction between the photoresist polymers.

The compounds of the present invention are cross-linkers of the chemical amplification type, and therefore further combine with the photoresist resin to generate acid ($H^+$) to induce continuous chain cross-linking. The exposed portion of the photoresist resin can be cured to a high density in the course of the post-baking step of the semi-conductor manufacturing process, thereby obtaining an excellent pattern with low exposure energy.

In addition, the hydroxyl groups generated by ring opening during the cross-linking process further participates in the cross-linking reaction, so that more effective cross-linking can be performed, and the photoresist can be cured to a higher density. Consequently, the solubility difference in developing solution between the exposed portion and the unexposed portion during the developing process becomes more pronounced so that a pattern having excellent profile can be obtained.

The photoresist cross-linker according to the present invention may be a homopolymer of the compound represented by Chemical Formula 1; however, it is more preferable that the cross-linker is a copolymer of (i) the compound represented by Chemical Formula 1 and (ii) one or more compound(s) selected from the group consisting of acrylate, methacrylate and maleic anhydride, as the second comonomer. The cross-linker copolymer may further comprises the compound of the following Chemical Formula 2 as the third monomer.

<Chemical Formula 2>

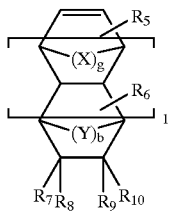

wherein, X and Y individually represent O, S or C; g and h individually represent a number of 1 or 2; l is a number of 0 to 5; $R_5$ and $R_6$ individually represent hydrogen or methyl; $R_7$, $R_8$, $R_9$ and $R_{10}$ individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group.

A preferred compound of Chemical Formula 2 is 5-norbornene-2-carboxylic acid.

Examples of cross-linkers according to the present invention are represented by following Chemical Formulas 3 to 5:

<Chemical Formula 3>

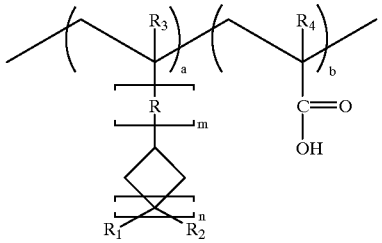

<Chemical Formula 4>

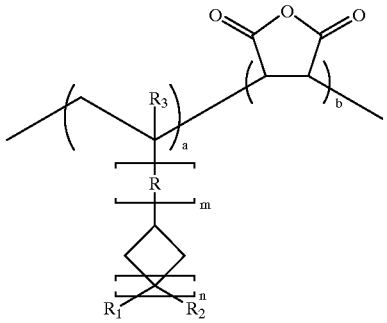

<Chemical Formula 5>

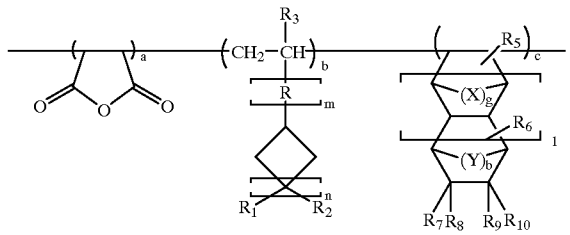

In the Formulas 3 to 5, X and Y individually represent O, S or C; g and h individually represent a number of 1 or 2; l is a number of 0 to 5; mn is a number of 0 or 1; n is a number of 1 to 5; $R_3$, $R_5$ and $R_6$ individually represent hydrogen or methyl; $R_1$, $R_2$, $R_7$, $R_8$, $R_9$, $R_{10}$ and R individually represent straight or branched $C_{1-10}$ alkyl, straight or branched $C_{1-10}$ ester, straight or branched $C_{1-10}$ ketone, straight or branched $C_{1-10}$ carboxylic acid, straight or branched $C_{1-10}$ acetal, straight or branched $C_{1-10}$ alkyl including at least one hydroxyl group, straight or branched $C_{1-10}$ ester including at least one hydroxyl group, straight or branched $C_{1-10}$ ketone including at least one hydroxyl group, straight or branched $C_{1-10}$ carboxylic acid including at least one hydroxyl group, and straight or branched $C_{1-10}$ acetal including at least one hydroxyl group, and a, b and c individually represent polymerization ratio of each comonomer. Preferably a: b=10–100 mol %: 0–90 mol % in Chemical Formula 3; a : b =10–90 mol %: 10–90 mol % in Chemical Formula 4; and a: b: c =0–90 mol %: 10–100 mol % : 0–90 mol % in Chemical Formula 5.

The reaction mechanism for the cross-linkers according to the present invention is described with reference to Reaction Scheme 1 shown below.

First, a cross-linker polymer according to the present invention is mixed with a photoresist resin, and the mixture is coated on a conventional semi-conductor substrate (stage 1). Then, when a predetermined region of the substrate is exposed to light, the exposed portion generates acid (stage 2). Due to the acid generated from the exposed portion, the cross-linker of the present invention and the photoresist combine together, and as a result of such cross-linking, acid is further generated. Since a cross-linkable hydroxyl group is regenerated on the cross-linker, continuous chain cross-linking is carried out (stage 3).

In the following Reaction Scheme 1, m of the Chemical Formula I is 0:

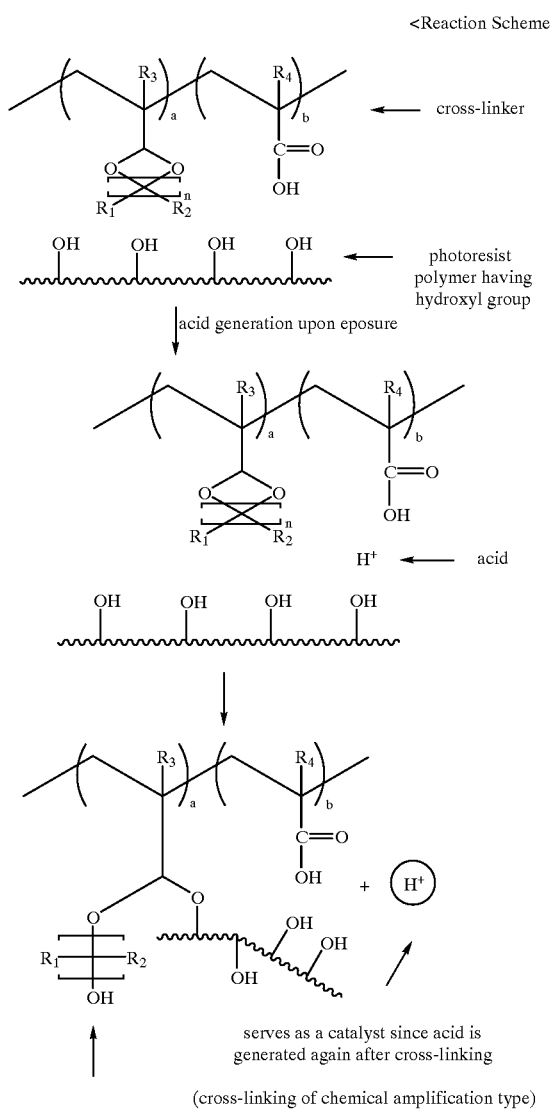

Preparation of Cross-linkers

Preparation of cross-linking polymers according to the present invention is specifically described in Examples 1 to 10 below.

Preparation of Photoresist Compositions and Formation of Photoresist Patterns

Since the cross-linkers of the present invention are chemical amplification type cross-linkers, photoresist compositions according to the present invention comprise (i) a negative photoresist resin, (ii) a cross-linker according to the present invention, and (iii) a photoacid generator, together with (iv) an organic solvent in which these substances are mixed.

As the photoacid generator, sulfide or onium type compounds are preferably used. For example, the photoacid generator may be one or more compounds selected from the group consisting of diphenyl iodide hexafluorophosphate, diphenyl iodide hexafluoroarsenate, diphenyliodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluoroantimonate, triphenylsulfonium triflate and dibutylnaphthylsulfonium triflate.

As an organic solvent, cyclohexanone, methyl 3-methoxypriopionate, ethyl 3-ethoxypropionate and/or propylene glycol methyl ether acetate may be used in a single solvent or a mixed solvent.

A photoresist composition prepared according to the present invention is spin-coated on a silicon wafer to form a thin film, and the film is "soft-baked" in an oven or on a hot plate at 70 to 200° C., more preferably at 100 to 170° C. for 1 to 5 minutes. Then, the photoresist film is exposed to light by using a deep ultraviolet exposer or an excimer laser exposer, and then "post-baked" at 10 to 200° C., more preferably, at 100 to 200° C. As a light source, ArF, KrF, E-beam, X-ray, EUV (extremely ultraviolet), DUV (deep ultraviolet) or the like may be used. The exposure energy is preferably 0.1 to 100 mJ/cm².

The exposed wafer is developed by impregnating the wafer in an alkaline developing solution such as 2.38 wt % or 2.5 wt % aqueous TMAH solution for a predetermined time, preferably for 1.5 minutes, to obtain an ultramicro pattern.

The novel cross-linkers according to the present invention, being a chemical amplification type cross-linkers, have excellent cross-linking ability at lower exposure energy. A photoresist composition comprising a cross-linker according to the present invention has high sensitivity and excellent curability at extremely short exposure wavelengths, especially at the wavelength of ArF (193 nm), thereby allowing a micro pattern having excellent profile to be obtained therefrom.

DESCRIPTION OF THE SPECIFIC EMBODIMENTS

The invention is described in more detail by referring to the examples below, but it should be noted that the present invention is not restricted to these examples.

EXAMPLE 1

Acrolein (30 g), AIBN (0.6 g) and tetrahydrofuran (75 g) were placed in a 200-ml flask, and reacted at 65° C. under nitrogen or argon atmosphere for 8 hours. After the polymerization was completed, polyacrolein was precipitated from ethyl ether (yield: 60%).

Polyacrolein thus obtained (20 g), ethane-1,2-diol (150 g), toluene-p-sulfonic acid (1 g) and benzene (200 g) were placed in a 1000-ml round-bottomed flask, and the reaction was performed under reflux with a Dean and Stark water separator attached to the flask, until no more water was generated. After the reaction was completed, the product was precipitated from distilled water, to obtain pure compound represented by following Chemical Formula 6a (yield: 45%).

<Chemical Formula 6a>

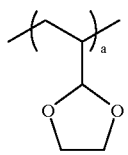

As the reaction catalyst, an acid such as trifluoromethanesulfonic acid, hydrochloric acid or boron trifluoride-etherate may be used instead of toluene-p-sulfonic acid. As a reaction solvent, a non-carbonyl solvent such as tetrahydrofuran may be used instead of benzene.

EXAMPLE 2

The procedure according to Example I was repeated but using propane-1,2-diol (20 g) instead of ethane-1,2-diol, to obtain the compound represented by Chemical Formula 7a (yield: 45%).

<Chemical Formula 7a>

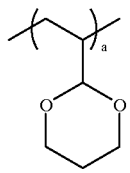

EXAMPLE 3

In a 100 ml flask, 2-vinyl-1,3-dioxolane (0.1 mole) of Chemical Formula 1a, acrylic acid (0.06 mole), tetrahydrofuran (20 g) and AIBN (0.2 g) were placed, and the mixture was reacted at 65° C. under nitrogen or argon atmosphere for 8 hours. After the polymerization was completed, the polymers were precipitated from distilled water or ethyl ether, to obtain the compound of Chemical Formula 6 (yield: 60%).

<Chemical Formula 1a>

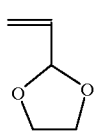

<Chemical Formula 6>

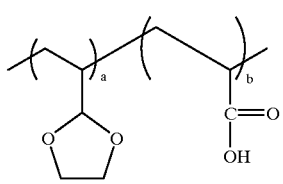

EXAMPLE 4

The procedure according to Example 3 was repeated but using 2-vinyl-1,3-dioxane (0.1 mole) of Chemical Formula 1b instead of 2-vinyl-1,3-dioxolane of Chemical Formula 1a, to obtain the compound represented by Chemical Formula 7 (yield: 55%).

<Chemical Formula 1b>

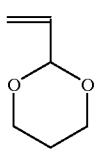

<Chemical Formula 7>

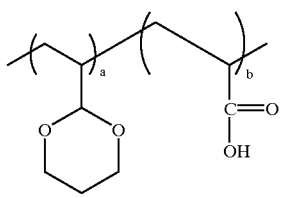

EXAMPLE 5

In a 250-ml flask, 2-vinyl-1,3-dioxolane (0.3 mole) of Chemical Formula 1a, maleic anhydride (0.1 mole), AIBN (0.8 g) and tetrahydrofuran (41 g) were placed, and the mixture was reacted at 65° C. under nitrogen or argon atmosphere for 8 hours. After the polymerization was completed, the polymers were precipitated from ethyl ether, and dried in vacuo to obtain pure compound of Chemical Formula 8 (yield: 80%).

As a polymerization initiator, conventional radical polymerization initiators such as lauryl peroxide may be used instead of AIBN (yield: 40%).

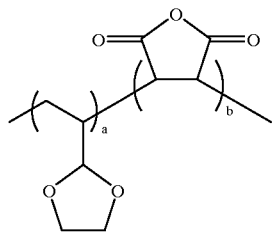

EXAMPLE 6

The procedure according to Example 5 was repeated but using 2-vinyl-1,3-dioxane (0.3 mole) of Chemical Formula 1b instead of 2-vinyl-1,3-dioxolane of Chemical Formula 1a, to obtain the compound represented by Chemical Formula 9 (yield: 42%).

<Chemical Formula 9>

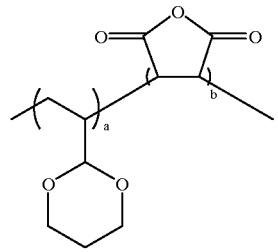

EXAMPLE 7

(Step 1)

0.5 mol of acrylic acid and 200 ml of THF were put into a 200 ml of flask. 0.12 mole of pyridine was added, and then 0.1 mole of 2-(2-bromoethyl)-1,3-dioxolane of Chemical Formula 20 was added. The mixture was reacted for 1 to 2 days. After completion of the reaction, white solid salts and solvent were discarded and the residue was distilled under reduced pressure to obtain a monomer of Chemical Formula 1c.

<Chemical Formula 20>

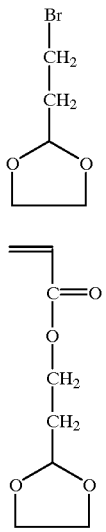

<Chemical Formula 1c>

(Step 2)

0.1 mole of crosslinking monomer of Formula 1c (the first monomer), 0 to 0.1 moles of maleic anhydride (the second monomer), and 0 to 0.5 moles of 5-norbornene-2-carboxylic acid (the third monomer):were mixed with 20 g of tetrahydrofuran in the presence of 0.2 g of polymerization initiator, AIBN, in a 200 ml flask. The mixture was reacted at 65° C. under nitrogen or argon for 8 hours. After completion of the polymerization, the resulting polymer was precipitated by ethyl ether solvent or distilled water to obtain the polymer of Chemical Formula 10.

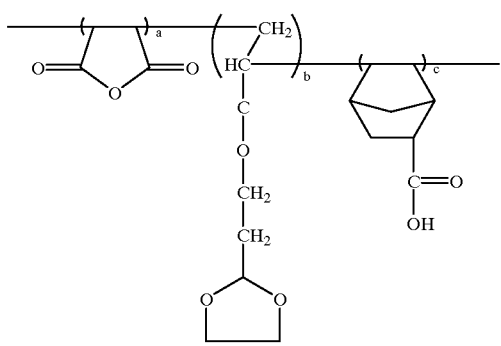

EXAMPLE 8

(Step 1)

The procedure according to Example 7 (Step 1) was repeated but using 2-(2-bromoethyl)-1,3-dioxane of Chemical Formula 21 instead of 2-(2-bromoethyl)-1,3-dioxolane of Chemical Formula 20, to obtain a monomer represented by Chemical Formula 1d.

<Chemical Formula 21>

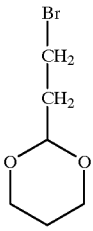

<Chemical Formula 1d>

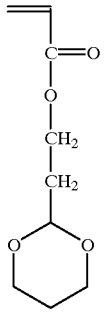

(Step 2)

The procedure according to Example 7 (Step 2) was repeated but using the monomer of Chemical Formula 1d instead of the monomer of Chemical Formula 1c, to obtain the polymer of Chemical Formula 11.

<Chemical Formula 11>

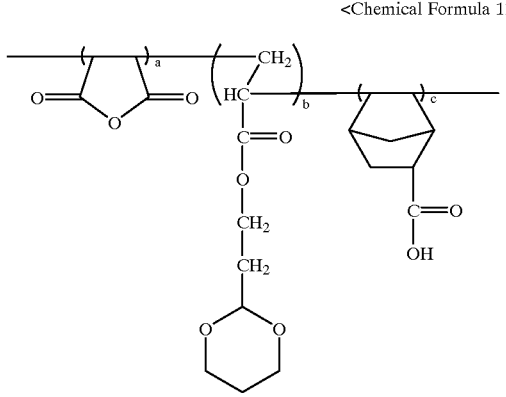

EXAMPLE 9

0.1 mole of crosslinking monomer of formula 1c obtained by Example 7 (Step 1), 0.2 g of AIBN, and 20 g of tetrahydrofuran were mixed in a 200 ml flask. The mixture was reacted at 65° C. under nitrogen or argon for 8 hours. After completion of the polymerization, the resulting polymer was precipitated by ethyl ether solvent or distilled water to obtain the crosslinking homopolymer of the Chemical Formula 12:

<Chemical Formula 12>

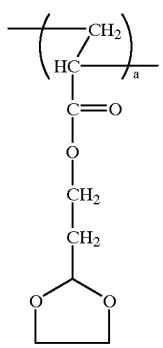

EXAMPLE 10

The procedure according to Example 9 was repeated but using the monomer of Chemical Formula 1d obtained by Example 8 (Step 1) instead of the monomer of Chemical Formula 1c, to obtain the crosslinking homopolymer of the Chemical Formula 13.

<Chemical Formula 13>

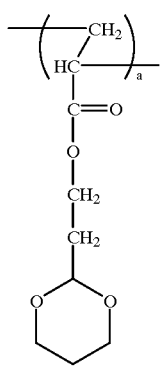

EXAMPLE 11

(i) The photoresist resin represented by following Chemical Formula 14, that is, poly(bicyclo[2.2.1]hept-5-ene/2-hydroxyethylbicyclo[2.2.1]hept-5-ene 2-carboxylate/maleic anhydride) (20 g), (ii) the cross-linker of Chemical Formula 6a obtained from Example 1 above (5 g), and (iii) triphenylsulfonium triflate as a photoacid generator (0.6 g) were dissolved in propylene glycol methyl ether acetate (200 g), to prepare a photoresist composition.

<Chemical Formula 14>

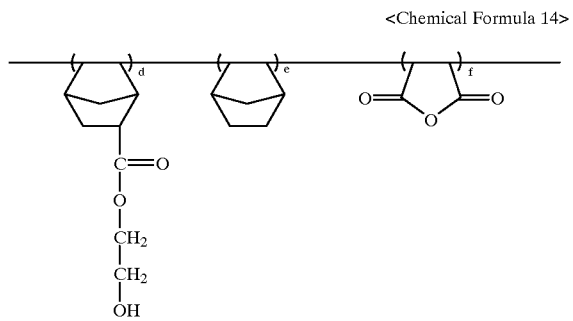

Figure 2:
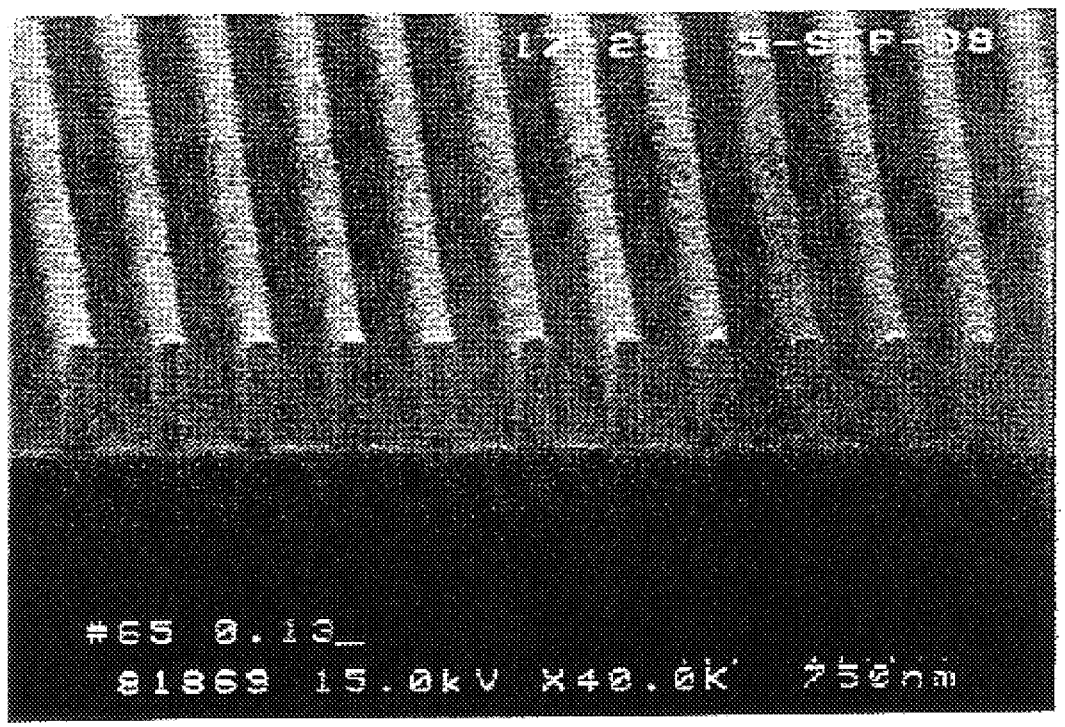
FIG. 2 to FIG. 5 show photoresist patterns prepared by using a cross-linker according to the present invention.

The photoresist composition thus prepared was coated on a silicon wafer, and soft-baked at 110° C. for 90 seconds, exposed to light by using ArF exposer, post-baked at 110° C. for 90 seconds, and then developed with 2.38 wt % TMAH developing solution. As a result, a 0.13 μm L/S ultramicro negative pattern was obtained as illustrated in FIG. 2.

The energy used for exposure was 18 mJ/cm$^2$. The curing sensitivity of the photoresist composition was excellent at such low intensity exposure energy and the swelling shown in FIG. 1 was not observed. These results are due to the excellent curability of poly(3,3-dimethoxypropene) resin, a cross-linker according to the present invention, and the intimate cross-linking resulting therefrom.

EXAMPLE 12

Figure 3:
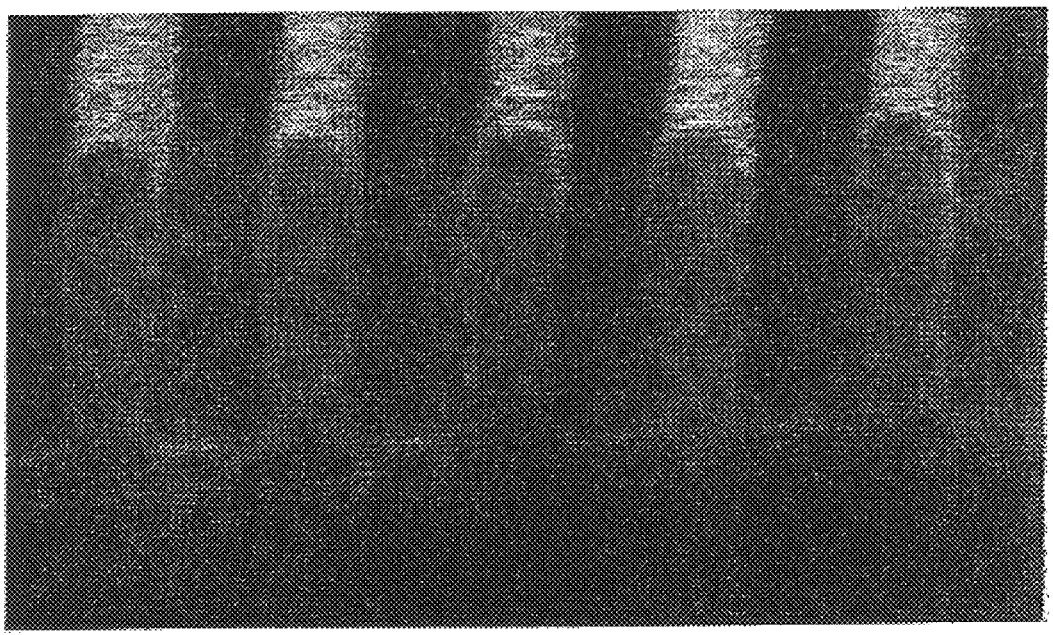

The procedure according to Example 11 was repeated but using the cross-linker of Chemical Formula 6b obtained from Example 2, instead of the cross-linker obtained from Example 1, to form a photoresist pattern. An ultramicro negative pattern of 0.13 μm L/S was obtained (FIG. 3).

EXAMPLE 13

The procedure according to Example 11 was repeated but using the cross-linker of Chemical Formula 6 obtained from Example 3, instead of the cross-linker obtained from Example 1, to form a photoresist pattern. An ultramicro negative pattern of 0.13 μm L/S was obtained.

EXAMPLE 14

The procedure according to Example 11 was repeated but using the cross-linker of Chemical Formula 7 obtained from Example 4, instead of the cross-linker obtained from Example 1, to form a photoresist pattern. An ultramicro negative pattern of 0.13 μm L/S was obtained.

EXAMPLE 15

Figure 4:
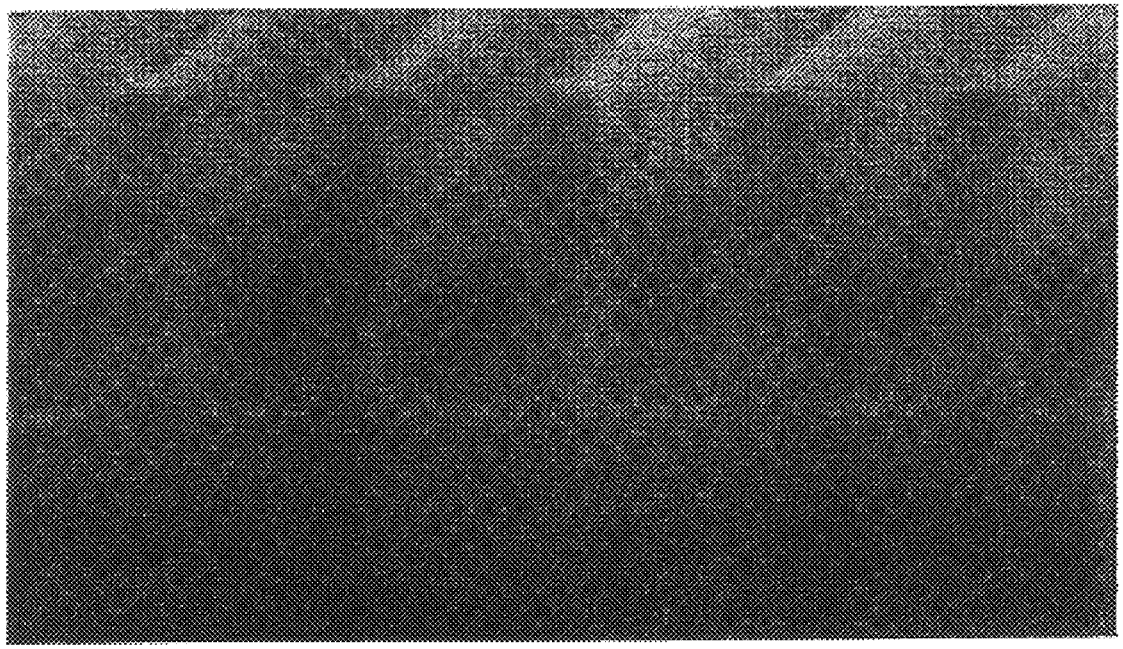

The procedure according to Example 11 was repeated but using the cross-linker of Chemical Formula 8 obtained from Example 5, instead of the cross-linker obtained from Example 1, to form a photoresist pattern. An ultramicro negative pattern of 0.13 μm L/S was obtained (FIG. 4).

EXAMPLE 16

Figure 5:
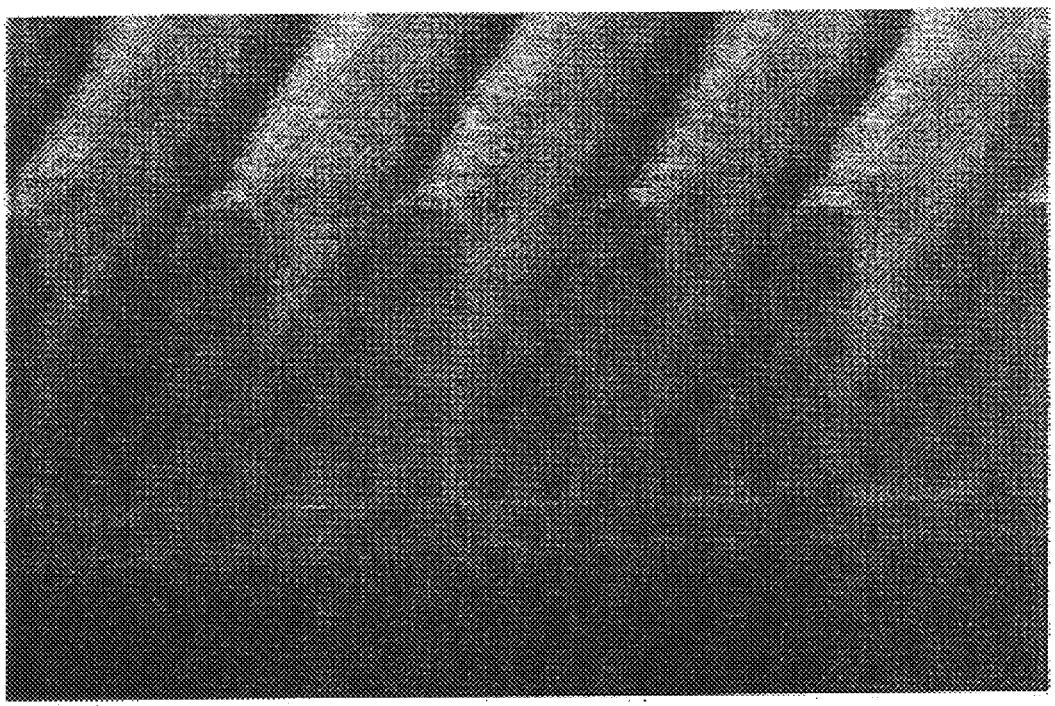

The procedure according to Example 11 was repeated but using the cross-linker of Chemical Formula 9 obtained from Example 6, instead of the cross-linker obtained from Example 1, to form a photoresist pattern. An ultramicro negative pattern of 0.13 μm L/S was obtained (FIG. 5).

EXAMPLE 17

The procedure according to Example 11 was repeated but using the cross-linker of Chemical Formula 10 obtained from Example 7 and photoresist resin of Chemical Formula 15, instead of the cross-linker obtained from Example 1 and photoresist resin of Chemical Formula 14, to form a photoresist pattern. An ultramicro negative pattern of 0.13 μm L/S was obtained.

<Chemical Formula 15>

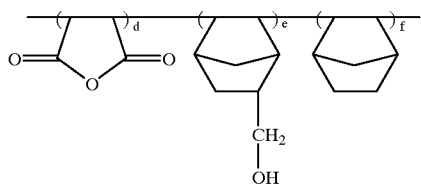

EXAMPLE 18

The procedure according to Example 17 was repeated but using the photoresist resin of Chemical Formula 16, instead of the photoresist resin of Chemical Formula 15, to form a photoresist pattern. An ultramicro negative pattern of 0.20 μm L/S was obtained.

<Chemical Formula 16>

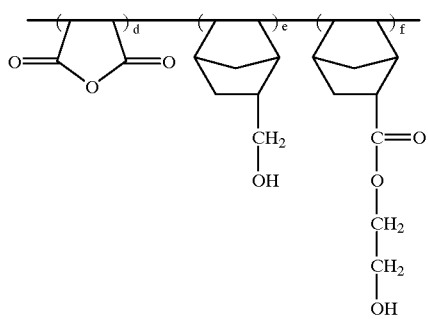

EXAMPLE 19

The procedure according to Example 17 was repeated but using the photoresist resin of Chemical Formula 17, instead of the photoresist resin of Chemical Formula 15, to form a photoresist pattern. An ultramicro negative pattern of 0.20 μm L/S was obtained.

<Chemical Formula 17>

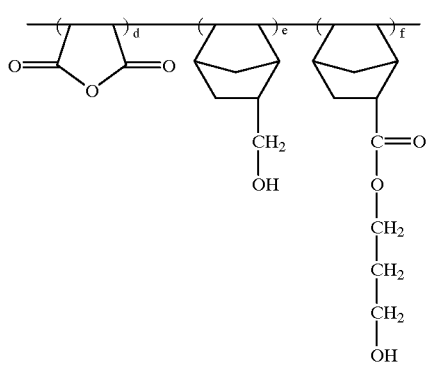

EXAMPLE 20

The procedure according to Example 17 was repeated but using the photoresist resin of Chemical Formula 18, instead of the photoresist resin of Chemical Formula 15, to form a photoresist pattern. An ultramicro negative pattern of 0.20 ↑m L/S was obtained.

<Chemical Formula 18>

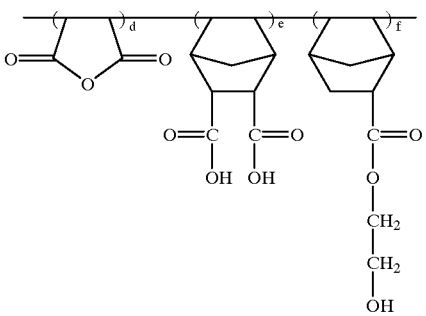

EXAMPLE 21

The procedure according to Example 17 was repeated but using the photoresist resin of Chemical Formula 19, instead of the photoresist resin of Chemical Formula 15, to form a photoresist pattern. An ultramicro negative pattern of 0.20 μm L/S was obtained.

<Chemical Formula 19>

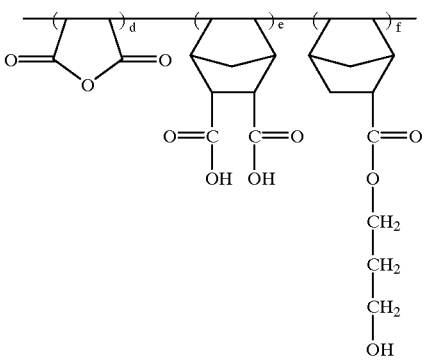

What is claimed is:

1. A photoresist cross-linker copolymer which comprises repeating units derived from:
   (i) a compound represented by following Chemical Formula 1:

<Chemical Formula 1>

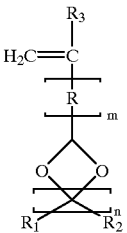

wherein,
R represents straight or branched $C_{1-10}$ alkylene optionally comprising an ester functional group, a ketone functional group, a carboxylic acid functional group, or an acetal functional group, or straight or branced $C_{1-10}$ alkylene comprising at least one hydroxyl group and optionally comprising an ester functional group, a ketone functional group, a carboxylic acid functional group or an acetal functional group;

$R_1$ and $R_2$ are independently hydrogen, straight or branched $C_{1-10}$ alkyl comprising an ester functional group, a ketone functional group, a carboxylic acid functional group or an acetal functional group, or straight or branched $C_{1-10}$ alkyl comprising at least one hydroxyl group and optionally comprising an ester functional group, a ketone functional group, a carboxylic acid functional group or an acetal functional group;

$R_3$ represents hydrogen or methyl;

m represents 0 or 1; and n represents a number of 1 to 5;

ii) one or more compounds selected from the group consisting of acrylic acid, methacrylic acid and maleic anhydride; and (iii) a compound represented by the following Chemical Formula 2:

<Chemical Formula 2>

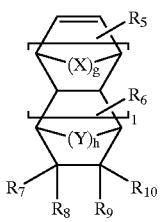

wherein,

X and Y individually represent O, S or C;

g and h individually represent a number of 1 or 2;

l is a number of 0 to 5;

$R_5$ and $R_6$ individually represent hydrogen or methyl; and $R_7$, $R_8$, $R_9$ and $R_{10}$ are independently straight or branched $C_{1-10}$ alkyl optionally comprising an ester functional group, a ketone functional group, a carboxylic acid functional group, or an acetal functional group, or straight or branched $C_{1-10}$ alkyl comprising at least one hydroxyl group and optionally comprising an ester functional group, a ketone functional group, a carboxylic acid functional group, or an acetal functional group.

2. A photoresist cross-linker copolymer according to claim 1, wherein the compound of Chemical Formula 2 is 5-norbornene-2-carboxylic acid.

3. A photoresist cross-linker copolymer according to claim 1 represented by the following Chemcial Formula 5:

<Chemical Formula 5>

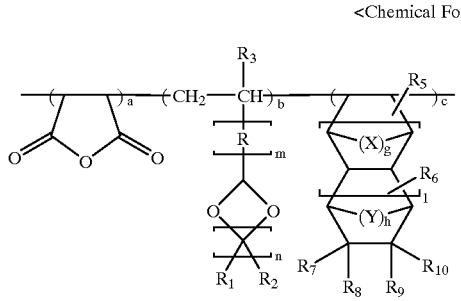

wherein, a, b and c individually represent the relative amounts of each comonomer and b and c are greater than 0.

4. A photoresist cross-linker according to claim 3 represented by one of the following Chemical Formulas 10 and 11:

<Chemical Formula 10>

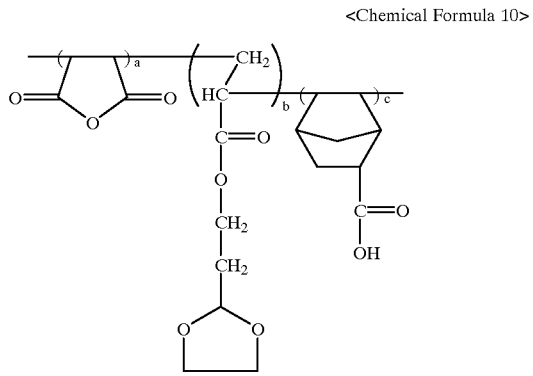

<Chemical Formula 11>

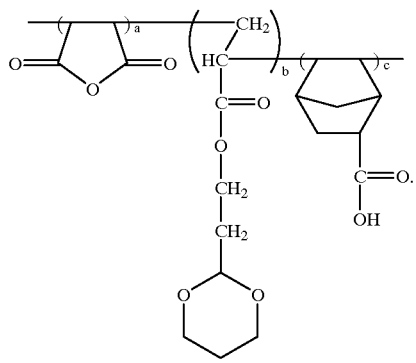

5. A negative photoresist composition which comprises (i) a cross-linker selected from the group consisting of a monomer represented by the following Chemical Formula 1, its homopolymer, its copolymers and mixtures thereof:

<Chemical Formula 1>

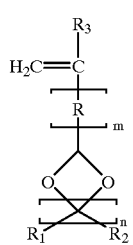

wherein,

R represents straight or branched $C_{1-10}$ alkylene optionally comprising an ester functional group, a ketone functional group, a carboxylic acid functional group, or an acetal functional group, or straight or branched $C_{1-10}$ alkylene comprising least one hydroxyl group and optionally comprising an ester functional group, a ketone functional group, a carboxylic acid functional group, or an acetal functional group;

$R_1$ and $R_2$ are independently hydrogen, straight or branched $C_{1-10}$ alkyl optionally comprising an ester functional group, a ketone functional group, a carboxylic acid functional group, or an acetal functional group, or straight or branched $C_{1-10}$ alkyl comprising at least one hydroxyl group and optionally comprising an ester functional group, a ketone functional group, a carboxylic acid functional group, or an acetal functional group;

$R_3$ represents hydrogen or methyl;

m represents 0 or 1; and n represents a number of 1 to 5; and (ii) a photoresist polymer having hydroxyl groups which are cross-linked by said cross-linker in the presence of acid.

6. A negative photoresist composition according to claim 5 further comprising (iii) a photoacid generator and (iv) an organic solvent.

7. A negative photoresist composition according to claim 6, wherein the photoresist polymer is selected from the group consisting of the compounds represented by following Chemical Formulas 14 to 19:

<Chemical Formula 14>

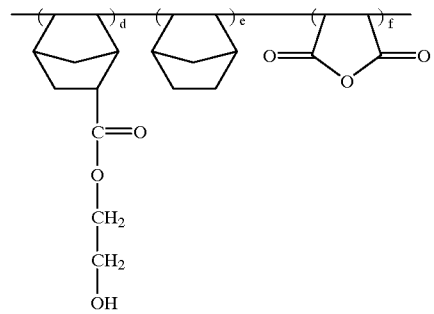

<Chemical Formula 15>

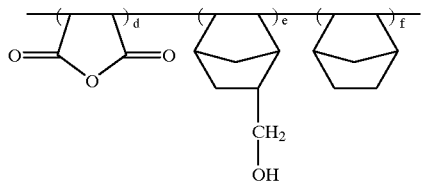

<Chemical Formula 16>

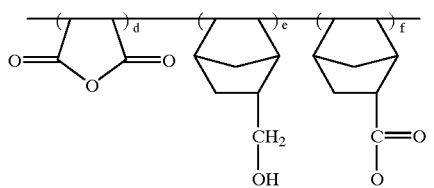

<Chemical Formula 17>

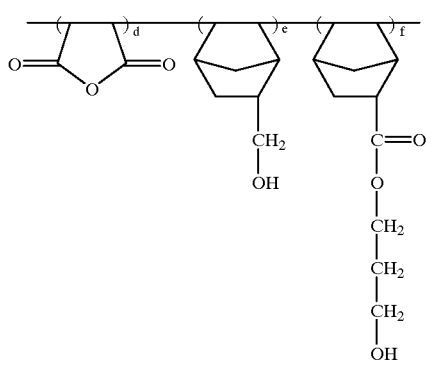

<Chemical Formula 18>

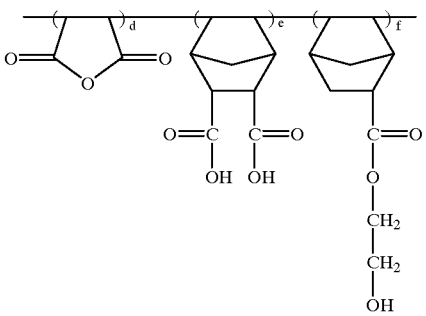

<Chemical Formula 19>

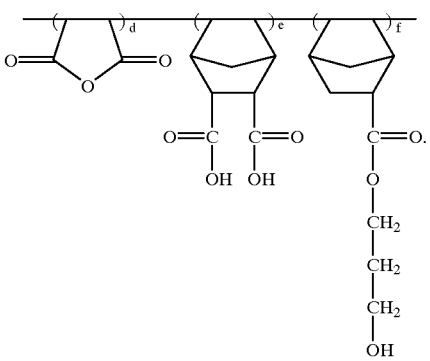

8. A negative photoresist composition according to claim 6, wherein the photoacid generator is one or more compound (s) selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluorophosphate, triphenylsulfonium hexafluoroarsenate, triphenylsulfonium hexafluorophosphate, triphenylsulfonium triflate and dibutylnaphthylsulfonium triflate.

9. A negative photoresist composition according to claim 6, wherein the organic solvent is selected from the group consisting of cyclohexanone, methyl 3-methoxypropionate, ethyl 3-ethoxypropionate and propylene glycol methyl ether acetate.

10. A process for forming a photoresist pattern, which comprises the steps of (a) coating the composition according to claim 5 on a wafer, (b) exposing the wafer to light by employing an exposer, and (c) developing the exposed wafer.

11. A process according to claim 10, wherein the light source is selected from the group consisting of ArF (193 nm), KrF (248 nm), E-beam, X-ray, EUV and DUV (deep ultraviolet).

12. A process according to claim 10, wherein the developing step is carried out by using an alkaline developing solution.

13. A process according to claim 12, wherein the alkaline developing solution is 2.38 wt. % or 2.5 wt. % aqueous TMAH solution.

14. A semiconductor element manufactured by the process according to claim 10.

15. A negative photoresist composition according to claim 5, wherein said cross-linker is selected from the group consisting of the compounds represented by the following chemical formulas 3, 4 and 5:

<Chemical Formula 3>

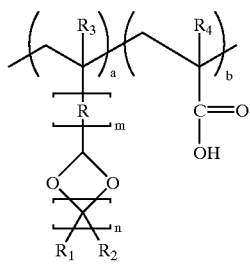

<Chemical Formula 4>

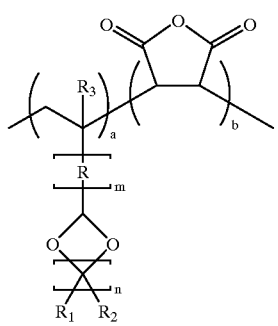

<Chemical Formula 5>

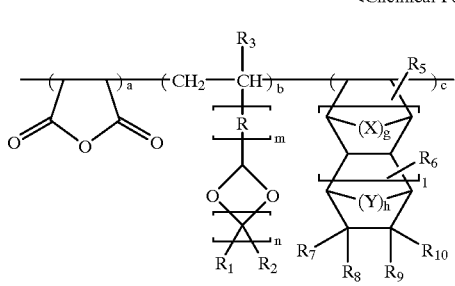

wherein,

X and Y individually represent O, S or C;

g and h individually represent a number of 1 or 2;

l is a number of 0 to 5;

m is a number of 0 or 1;

n is a number of 1 to 5;

$R_3$, $R_5$ and $R_6$ are independently hydrogen or methyl;

$R_1$, $R_2$, $R_7$, $R_8$, $R_9$, and $R_{10}$ are independently straight or branched $C_{1-10}$ alkyl optionally comprising an ester functional group, a ketone functional group, a carboxylic acid functional group, or an acetal functional group, or straight or branched $C_{1-10}$ alkyl comprising at least one hydroxyl group and optionally comprising an ester functional group, a ketone functional group, a carboxylic acid functional group or an acetal functional group;

R is straight or branched $C_{1-10}$ alkylene optionally comprising an ester functional group, a ketone functional group, a carboxylic acid functional group, or an acetal functional group, or straight or branched $C_{1-10}$ alkylene comprising at least one hydroxyl group and optionally comprising an ester functional group, a ketone functional group, a carboxylic acid functional group or an acetal functional group; and a, b and c individually represent the relative amounts of each comonomer, with b and c being greater then 0.

16. A negative photoresist composition according to claim 5, wherein said cross-linker is selected from the group consisting of the compounds represented by the following chemical formulas 1a, 1b, 1c, 1d and 6–13:

<Chemical Formula 1a>

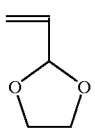

<Chemical Formula 1b>

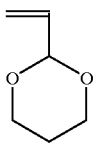

<Chemical Formula 1c>

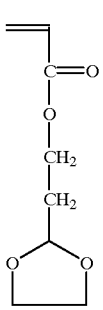

<Chemical Formula 1d>

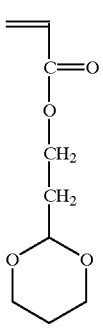

<Chemical Formula 6>

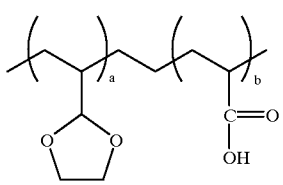

<Chemical Formula 7>
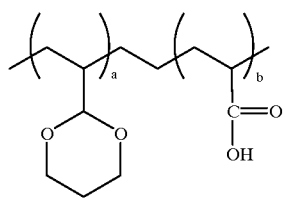
<Chemical Formula 8>
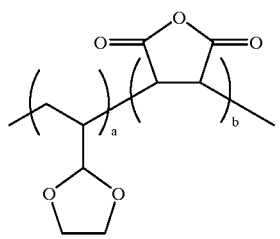
<Chemical Formula 9>
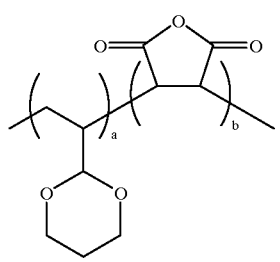
<Chemical Formula 10>
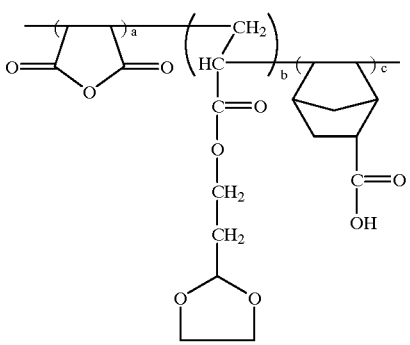
<Chemical Formula 11>
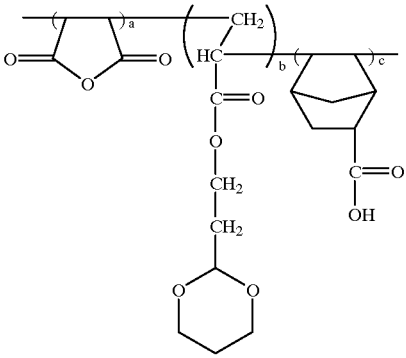
<Chemical Formula 12>
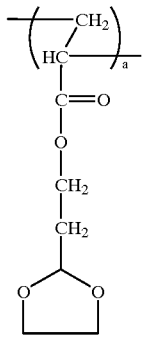
<Chemical Formula 13>
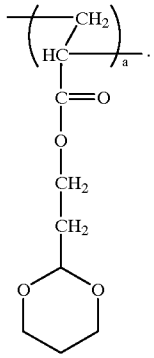
* * * * *

UNITED STATES PATENT AND TRADEMARK OFFICE
CERTIFICATE OF CORRECTION

PATENT NO. : 6,482,565 B1
DATED : November 19, 2002
INVENTOR(S) : Jae Chang et al.

It is certified that error appears in the above-identified patent and that said Letters Patent is hereby corrected as shown below:

Column 2,
Lines 18-28, please replace Chemical Formula 1 with the following Chemical Formula 1: --

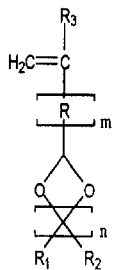

--.

Lines 65-66, the phrase "represented by the following Chemical Formula I have appropriate properties to serve as monomers" should read -- represented by the following Chemical Formula 1 have appropriate properties to serve as monomers --.

Column 3,
Lines 1-10, please replace Chemical Formula 1 with the following Chemical Formula 1:
--

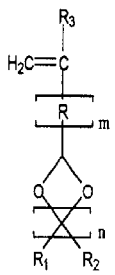

--.

Lines 55-65, please replace Chemical Formula 2 with the following Chemical Formula 2: --

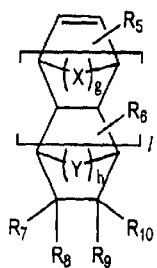

--.

UNITED STATES PATENT AND TRADEMARK OFFICE
CERTIFICATE OF CORRECTION

PATENT NO. : 6,482,565 B1
DATED : November 19, 2002
INVENTOR(S) : Jae Chang et al.

It is certified that error appears in the above-identified patent and that said Letters Patent is hereby corrected as shown below:

Column 4,
Lines 30-40, please replace Chemical Formula 4 with the following Chemical Formula 4: --

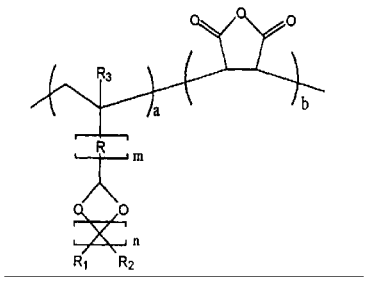

Lines 43-50, please replace Chemical Formula 5 with the following Chemical Formula 5:
--

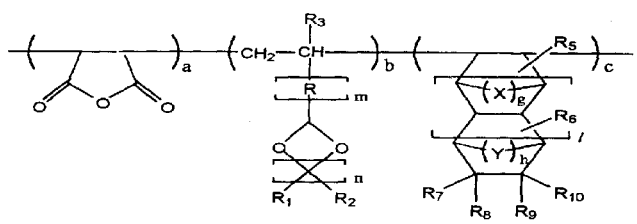

--.

Line 54, the phrase "I is a number of 0 to 5;" should read -- $l$ is a number of 0 to 5; --.

Column 5,
Lines 19-20, the phrase "In the following Reaction Scheme 1, m of the Chemical Formula 1 is 0:" should read -- In the following Reaction Scheme 1, m of the Chemical Formula 1 is 0: --.

UNITED STATES PATENT AND TRADEMARK OFFICE
CERTIFICATE OF CORRECTION

PATENT NO. : 6,482,565 B1
DATED : November 19, 2002
INVENTOR(S) : Jae Chang et al.

It is certified that error appears in the above-identified patent and that said Letters Patent is hereby corrected as shown below:

Column 5 (cont'd),
Lines 20-59, please replace Reaction Scheme 1 with the following Reaction Scheme 1:

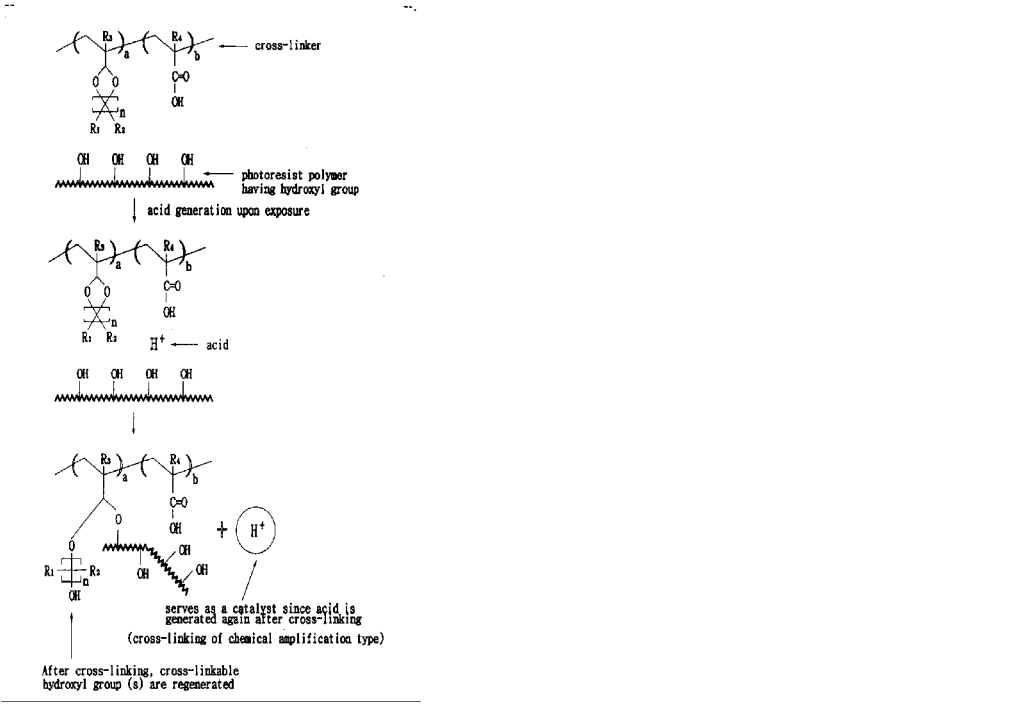

Column 7,
Line 26, the phrase "The procedure according to Example I was repeated" should read
-- The procedure according to Example 1 was repeated --.

Column 10,
Lines 31-34, the paragraph "The procedure according to Example 7 (Step 2) was repeated but using the monomer of Chemical Formula Id instead of the monomer of Chemical Formula Ic, to obtain the polymer of Chemical Formula 11." should read
-- The procedure according to Example 9 (Step 2) was repeated but using the monomer of Chemical Formula 1d instead of the monomer of Chemical Formula 1c, to obtain the polymer of Chemical Formula 11 --.

UNITED STATES PATENT AND TRADEMARK OFFICE
CERTIFICATE OF CORRECTION

PATENT NO. : 6,482,565 B1
DATED : November 19, 2002
INVENTOR(S) : Jae Chang et al.

It is certified that error appears in the above-identified patent and that said Letters Patent is hereby corrected as shown below:

Column 13,
Lines 66-67, the sentence "An ultramicro negative pattern of 0.20 ↑m L/S was obtained." should read -- An ultramicro negative pattern of 0.20 µm L/S was obtained. --

Column 17,
Lines 7-9, the claim "A negative photoresist comprosition according to claim 5 further comprising (iii) a photoacid generator and (iv) an organic solvent." should read -- A negative photoresist composition according to claim 5 further comprising (iii) a photoacid generator and (iv) an organic solvent. --

Column 20,
Lines 8-9, the phrase "a, b and c individually represent the relative amounts of each comonomer, with b and c being greater then 0." should read -- a, b and c individually represent the relative amounts of each comonomer, with b and c being greater than 0. --
Lines 60-66, please replace Chemical Formula 6 with the following Chemical Formula 6:

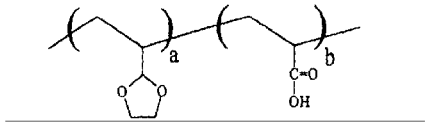

Column 21,
Lines 3-10, please replace Chemical Formula 7 with the following Chemical Formula 7:

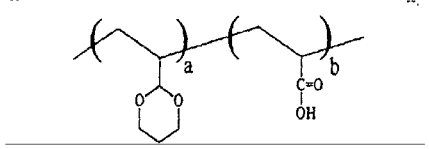

UNITED STATES PATENT AND TRADEMARK OFFICE
CERTIFICATE OF CORRECTION

PATENT NO. : 6,482,565 B1
DATED : November 19, 2002
INVENTOR(S) : Jae Chang et al.

It is certified that error appears in the above-identified patent and that said Letters Patent is hereby corrected as shown below:

<u>Column 25,</u>
Line 45, the phrase "to produce a photoresist polytechnic unit of the formula:" should read -- to produce a photoresist polymeric unit of the formula: --.

Signed and Sealed this

Seventeenth Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,482,565 B1
DATED        : November 19, 2002
INVENTOR(S)  : Jae Chang et al.

It is certified that error appears in the above-identified patent and that said Letters Patent is hereby corrected as shown below:

Column 2,
Lines 18-28, please replace Chemical Formula 1 with the following Chemical Formula 1: -- --.

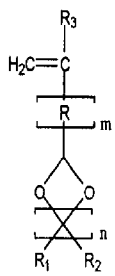

Lines 65-66, the phrase "represented by the following Chemical Formula I have appropriate properties to serve as monomers" should read -- represented by the following Chemical Formula 1 have appropriate properties to serve as monomers --.

Column 3,
Lines 1-10, please replace Chemical Formula 1 with the following Chemical Formula 1: -- --.

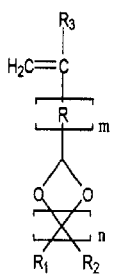

Lines 55-65, please replace Chemical Formula 2 with the following Chemical Formula 2: -- --.

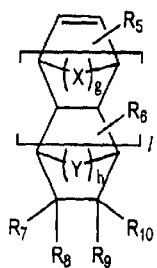

UNITED STATES PATENT AND TRADEMARK OFFICE
CERTIFICATE OF CORRECTION

PATENT NO.    : 6,482,565 B1
DATED         : November 19, 2002
INVENTOR(S)   : Jae Chang et al.

It is certified that error appears in the above-identified patent and that said Letters Patent is hereby corrected as shown below:

Column 4,
Lines 30-40, please replace Chemical Formula 4 with the following Chemical Formula 4: --

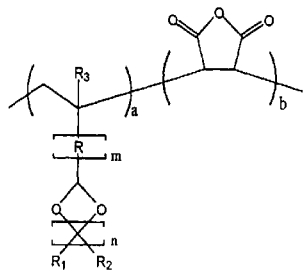

Lines 43-50, please replace Chemical Formula 5 with the following Chemical Formula 5:
--

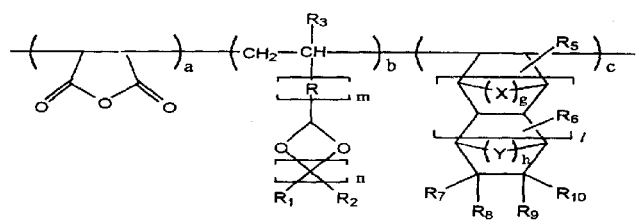

--.

Line 54, the phrase "I is a number of 0 to 5;" should read -- $l$ is a number of 0 to 5; --.

Column 5,
Lines 19-20, the phrase "In the following Reaction Scheme 1, m of the Chemical Formula 1 is 0:" should read -- In the following Reaction Scheme 1, m of the Chemical Formula 1 is 0: --.

UNITED STATES PATENT AND TRADEMARK OFFICE
CERTIFICATE OF CORRECTION

PATENT NO. : 6,482,565 B1  Page 3 of 5
DATED : November 19, 2002
INVENTOR(S) : Jae Chang et al.

It is certified that error appears in the above-identified patent and that said Letters Patent is hereby corrected as shown below:

Column 5 (cont'd),
Lines 49-59, please replace Reaction Scheme 1 with the following Reaction Scheme 1:

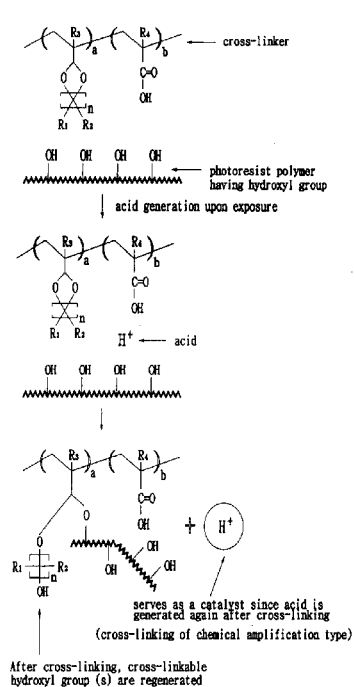

Column 7,
Line 26, the phrase "The procedure according to Example I was repeated" should read
-- The procedure according to Example 1 was repeated --.

Column 10,
Lines 31-34, the paragraph "The procedure according to Example 7 (Step 2) was repeated but using the monomer of Chemical Formula Id instead of the monomer of Chemical Formula Ic, to obtain the polymer of Chemical Formula 11." should read
-- The procedure according to Example 7 (Step 2) was repeated but using the monomer of Chemical Formula 1d instead of the monomer of Chemical Formula 1c, to obtain the polymer of Chemical Formula 11 --.

UNITED STATES PATENT AND TRADEMARK OFFICE
CERTIFICATE OF CORRECTION

PATENT NO. : 6,482,565 B1
DATED : November 19, 2002
INVENTOR(S) : Jae Chang et al.

It is certified that error appears in the above-identified patent and that said Letters Patent is hereby corrected as shown below:

Column 13,
Lines 66-67, the sentence "An ultramicro negative pattern of 0.20 ↑m L/S was obtained." should read -- An ultramicro negative pattern of 0.20 µm L/S was obtained. --

Column 17,
Lines 7-9, the claim "A negative photoresist comprosition according to claim 5 further comprising (iii) a photoacid generator and (iv) an organic solvent." should read -- A negative photoresist composition according to claim 5 further comprising (iii) a photoacid generator and (iv) an organic solvent. --

Column 20,
Lines 8-9, the phrase "a, b and c individually represent the relative amounts of each comonomer, with b and c being greater then 0." should read -- a, b and c individually represent the relative amounts of each comonomer, with b and c being greater than 0. --
Lines 60-66, please replace Chemical Formula 6 with the following Chemical Formula 6:

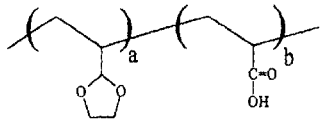

UNITED STATES PATENT AND TRADEMARK OFFICE
CERTIFICATE OF CORRECTION

PATENT NO. : 6,482,565 B1
DATED : November 19, 2002
INVENTOR(S) : Jae Chang et al.

It is certified that error appears in the above-identified patent and that said Letters Patent is hereby corrected as shown below:

Column 21,
Lines 3-10, please replace Chemical Formula 7 with the following Chemical Formula 7:

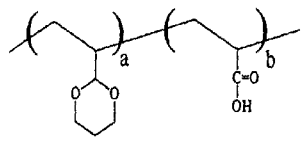

This certificate supersedes Certificate of Correction issued August 17, 2004.

Signed and Sealed this

Seventh Day of December, 2004

JON W. DUDAS
*Director of the United States Patent and Trademark Office*